United States Patent [19]
Getzinger et al.

[11] Patent Number: 5,640,956
[45] Date of Patent: Jun. 24, 1997

[54] METHODS AND APPARATUS FOR CORRELATING ULTRASONIC IMAGE DATA AND RADIOGRAPHIC IMAGE DATA

[75] Inventors: Thomas W. Getzinger, Bellevue; Ascher Shmulewitz, Mercer Island, both of Wash.

[73] Assignee: Neovision Corporation, Seattle, Wash.

[21] Appl. No.: 474,375

[22] Filed: Jun. 7, 1995

[51] Int. Cl.$^6$ .................................. A61B 8/00; A61B 5/05
[52] U.S. Cl. .............................. 128/653.1; 128/660.01; 128/660.04
[58] Field of Search .................... 128/653.1, 660.01, 128/660.03, 660.04, 660.09, 915

[56] References Cited

U.S. PATENT DOCUMENTS

| | | | |
|---|---|---|---|
| 3,765,403 | 10/1973 | Brenden | 128/2 V |
| 4,434,799 | 3/1984 | Taenzer | 128/660 |
| 5,411,026 | 5/1995 | Carol | 128/660.03 |
| 5,447,154 | 9/1995 | Cinquin et al. | 128/653.1 |

FOREIGN PATENT DOCUMENTS

| | | | |
|---|---|---|---|
| WO83/02053 | 6/1983 | WIPO | A61B 10/00 |
| WO94/21189 | 9/1994 | WIPO | A61B 68/08 |

OTHER PUBLICATIONS

R.F. Brem and O.M.B. Gatewood, "Template–guided Breast US", *Radiology*, Sep. 1992, pp. 872–874.

B.D. Fornage et al., "Ultrasound–Guided Needle Biopsy Of The Breast And Other Interventional Procedures," *Radiologic Clinics Of North America*, vol. 30, No. 1, Jan. 1992, pp. 167–185.

W.F. Conway et al., "Occult Breast Masses: Use of a Mammographic Localizing Grid for US Evaluation", *Radiology*, Oct. 1991, pp. 143–146.

E.B. Mendelson, "Ultrasound secures place in breast Ca management", *Diagnostic Imaging*, Apr. 1991, pp. 120–129.

*Primary Examiner*—Francis Jaworski
*Assistant Examiner*—Derrick Fields
*Attorney, Agent, or Firm*—Fish & Neave; Nicola A. Pisano

[57] ABSTRACT

Apparatus and methods are provided for correlating radiologic and ultrasonic images of biological tissue. An X-ray image and a plurality of corresponding ultrasound images are generated while the biological tissue remains immobilized. X-ray opaque indexing points provide lateral registration of the X-ray film with the ultrasound apparatus. The fan-out of X-ray beams penetrating the tissue from a point X-ray source is determined and used to correlate the X-ray image data to the ultrasonic image data. Apparatus and methods are also provided for determining the location of the X-ray source relative to the indexing points.

18 Claims, 10 Drawing Sheets

METHODS AND APPARATUS FOR CORRELATING ULTRASONIC IMAGE DATA AND RADIOGRAPHIC IMAGE DATA

This invention relates to methods and apparatus for imaging breast tissue employing both X-ray and ultrasound technology to provide enhanced diagnostic capability. In particular, the present invention provides methods and apparatus for correlating X-ray images and ultrasonic image data.

BACKGROUND OF THE INVENTION

The use of X-ray technology for providing two-dimensional images of breast tissue for diagnosis of carcinoma or other abnormalities is well known. X-ray imaging has a number of limitations which are universally recognized by radiologists. In particular, X-ray imaging of breast tissue has the inherent limitation that a mammogram provides only a two-dimensional image of a three-dimensional object. Thus, although a potential area of concern may be indicated on a mammogram, the elevation of the subject area within the breast may be uncertain, leading to a biopsy of broader scope than would otherwise be necessary.

As an alternative to conventional mammography, apparatus has been developed that employs ultrasound technology for breast tissue imaging. Ultrasound imaging devices display echoes received from a piezoelectric transducer as brightness levels proportional to the backscattered echo amplitude. The brightness levels are displayed at the appropriate echo range and transducer position or orientation, resulting in cross-sectional images of the object in a plane perpendicular to the transducer emitting face.

It has long been recognized that ultrasound imaging of breast tissue provides some information about internal breast structures that can be obtained only imperfectly, or not at all, with conventional mammography. Thus, there has been a longfelt need to augment the information obtained by mammography with ultrasonic imaging, using either dedicated ultrasound apparatus as described, for example, in Brenden, U.S. Pat. No. 3,765,403, and Taenzer, U.S. Pat. No. 4,434,799, or free-hand techniques, described, for example, in Mendelson, "Ultrasound Secures Place In Breast Ca Management", *Diagnostic Imaging*, April 1991, pp. 120–129.

A drawback common to the use of both dedicated ultrasonic apparatus and freehand ultrasound examinations to supplement mammography is the inability to provide geometric registration between the mammogram and ultrasound images. This lack of registration results from movement of the breast tissue (and its internal structures) between the compressed shape induced by the mammography apparatus and the shape induced by the dedicated ultrasound apparatus, or in the case of freehand ultrasound examination, direct palpation of the breast tissue.

Conway, "Occult Breast Masses: Use Of A Mammographic Localizing Grid For US Evaluation", *Radiology*, 181:143–146 (1991) and Brem and Gatewood, "Template Guided Breast Ultrasound", *Radiology*, 184:872–874 (1992), describe attempts to achieve spatial registration between a mammogram and an ultrasound image by substituting the compression plate, after the mammogram is taken, with a cut-open compression plate that allows insertion of a manually manipulated ultrasound transducer.

The approach described in the above-mentioned articles has several practical drawbacks, including marking the patient's breast with an indelible pen, the increased length of the procedure, the need to have the mammographer present to ensure correct repositioning the patient's breast on the localization grid after the compression plate (used in mammography) is replaced by the cut-open compression plate, and the need for a priori knowledge of where the location of any suspected lesion. Moreover, as noted in the Conway article, even the use of indelible markings on the patient's skin cannot prevent movement of the underlying breast tissue.

In response to longfelt, but unsatisfied, need to provide registered radiologic and ultrasonic image data, the sono-mammography methods and apparatus described in co-pending and commonly assigned U.S. patent application Ser. Nos. 08/145,958, filed Oct. 29, 1993, and 08/277,894, filed Jul. 20, 1994, were developed. Those applications describe combined radiologic and ultrasonic imaging apparatus wherein breast tissue remains immobilized while sequentially exposed to both X-rays and ultrasound. Apparatus described as having similar functionality is also disclosed in International Application WO 94/21189.

Applicants have observed, however, that even for apparatus as described in the above applications, wherein the breast tissue remains immobilized during sequential exposure to radiologic and ultrasound imaging, it is still possible to observe regions of the breast where the ultrasound image appears poorly to correlate to the X-ray image.

In view of the foregoing, it would be desirable to provide apparatus and methods for providing ultrasound images of breast tissue that are correlated to an X-ray image of the breast tissue.

It would be still further desirable to provide apparatus and methods capable of correlating geometrically registered X-ray and ultrasound images to provide holographic views of a patient's breast tissue.

SUMMARY OF THE INVENTION

In view of the foregoing, it is an object of the present invention to provide apparatus and methods for creating ultrasound images of breast tissue that are correlated to an X-ray image of the breast tissue.

It is a still further object of the invention to provide apparatus and methods capable of correlating geometrically registered X-ray and ultrasound images to provide holographic views of a patient's breast tissue.

These and other objects of the invention are accomplished in accordance with the principles of the invention by providing methods and apparatus for correlating geometrically registered X-ray and ultrasound images. In accordance with the present invention, apparatus is provided for first evaluating the point-source behavior of the X-ray source. Reference markers are provided for geometrically aligning the ultrasonic image data with the X-ray data obtained during examination of biological tissue, to account for misalignment between the X-ray image receptor and the ultrasonic transducer. Then, using the data on the point source behavior of the X-ray source, and correcting for any misalignment between the X-ray image receptor and the ultrasonic image data, the ultrasonic image data is resampled using digital image warping techniques to account for imaging artifacts present in X-ray image resulting from the point-source behavior of the X-ray imaging apparatus.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

Figure 1A:
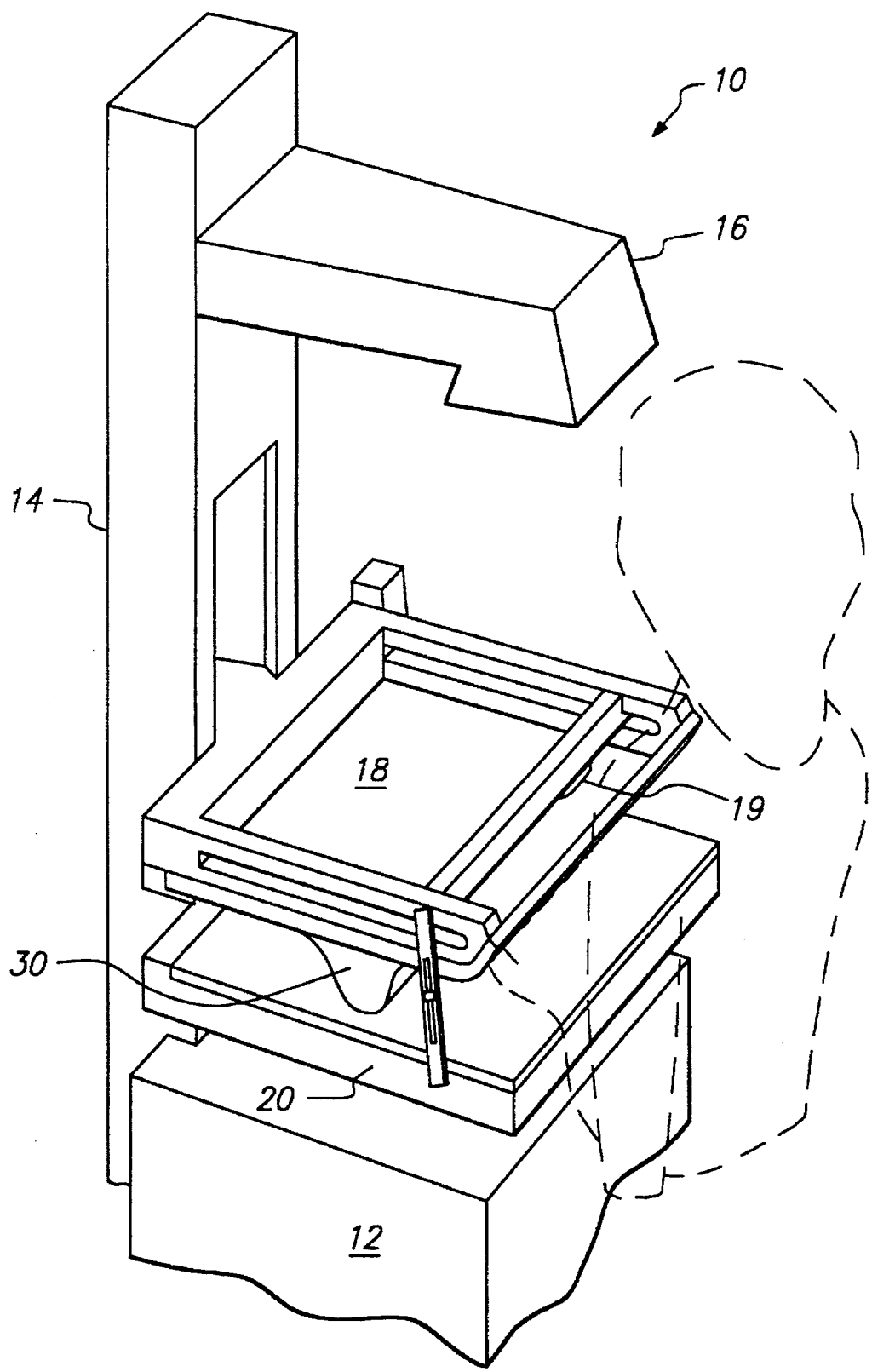
FIGS. 1A and 1B are, respectively, a side elevation of a sonomammography apparatus and a partial side elevation of the sonomammography apparatus of FIG. 1A as used during a breast examination.
Figure 1B:
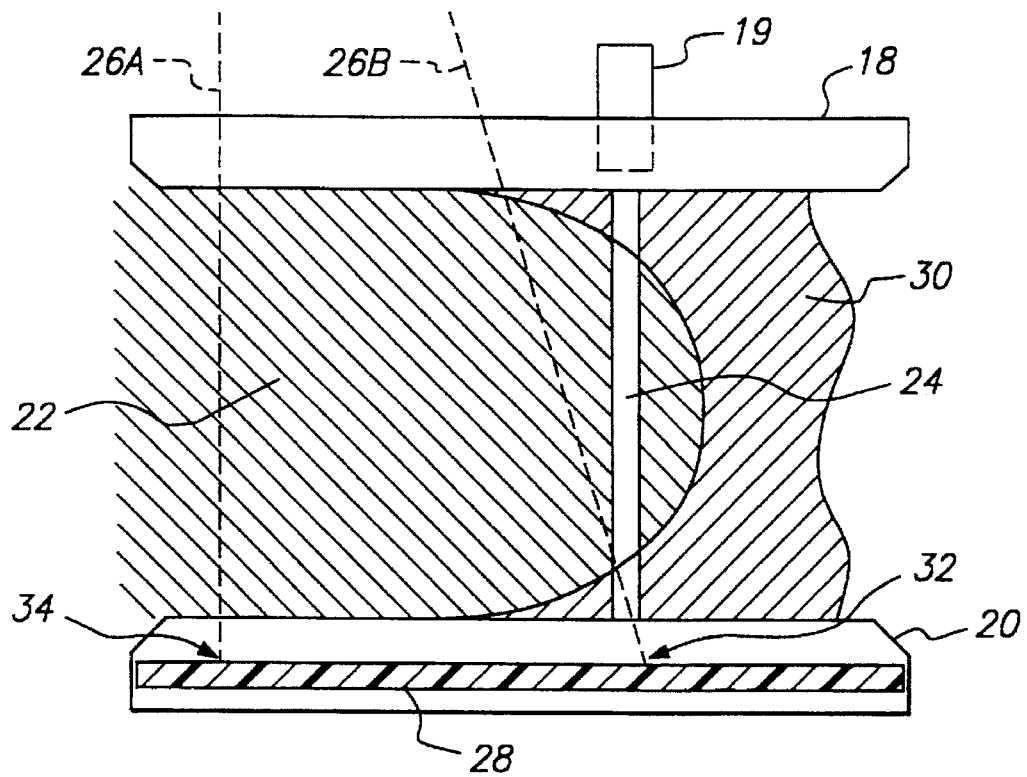

Referring to FIGS. 1A and 1B, illustrative sonomammography apparatus 10 is briefly described. Sonomammography apparatus 10 comprises base 12, vertical column 14, top assembly 16, upper compression plate 18, ultrasound transducer 19 and lower compression plate, diffraction grid and film cassette 20 (collectively referred to as a "Bucky"). Further details of the construction of sonomammography apparatus 10 are disclosed in copending and commonly assigned U.S. patent application Ser. Nos. 08/145,958, filed Oct. 29, 1993, and 08/277,894, filed Jul. 20, 1994, which are incorporated herein by reference in their entireties.

When using sonomammography apparatus 10, to examine a patient's tissue, breast tissue 22 is compressed between upper compression plate 18 and Bucky 20. Ultrasound transducer 19 is used to obtain ultrasonic data at multiple locations comprising a grid of sample points. At each point in the grid a narrow beam of ultrasonic energy is transmitted into the tissue being examined and energy is reflected (echoed) by various structures within the tissue. The reflected energy is received, sampled, quantized, and stored for later processing.

Figure 2:
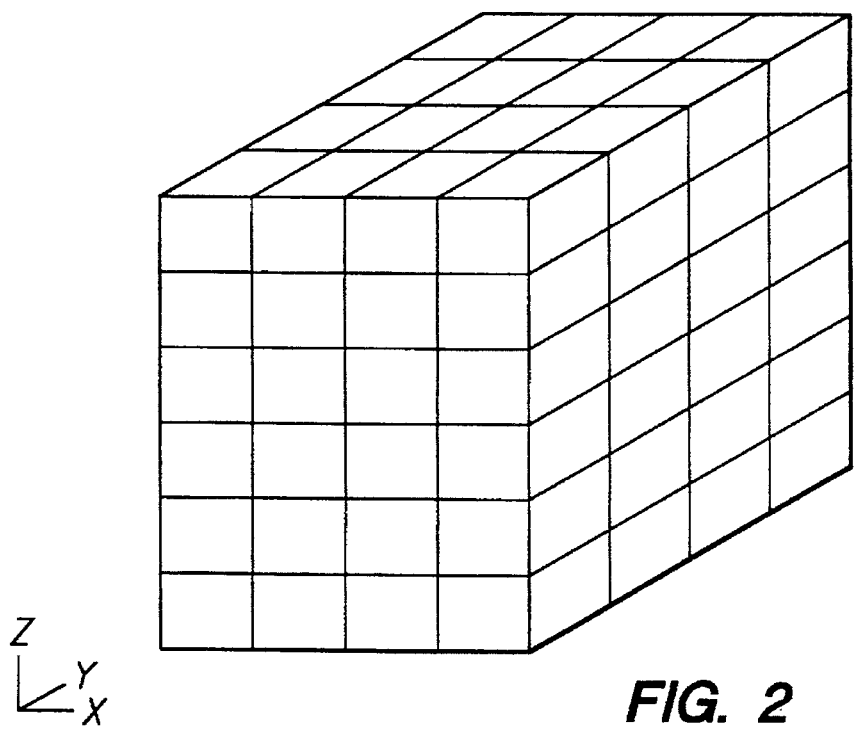
FIG. 2 illustrates the volume sampling obtained by the ultrasonic data of the breast tissue.

As shown in FIG. 2, the stored ultrasonic data comprises a three-dimensional volume sampling of the tissue being examined. Each column in FIG. 2 comprises data obtained at a single sample point by transducer 20, and each cube in a sample column comprises a single sample of reflected ultrasonic energy. By assembling adjacent cubes in a plane, ultrasonic images, or "slices" are created parallel to the xy, yz, or xz coordinate planes. These cubes are orthogonal in nature, are oriented in mutually parallel space apart planes, and fill all of the volume scanned (i.e., there are no gaps between the cubes).

Referring again to FIG. 1B, an X-ray image of breast 22 is also obtained by exposing breast tissue 22 to an X-ray source (not shown) while tissue 22 is in the same position as it was while the ultrasonic data was being gathered. X-ray radiation, illustratively denoted by X-ray beams 26A and 26B, passes through compression plate 18, breast tissue 22 and Bucky 20 to expose X-ray film 28. In accordance with the principles of the present invention, X-ray film 28 is then developed and the X-ray image scanned and digitized for storage and processing. Alternatively, a digital X-ray receptor may be used instead of X-ray film 28, so that the digitized X-ray image is obtained directly without the need to develop and digitize an image exposed on conventional X-ray film.

Gel pad 30 contacts the frontal area of the patient's breast, i.e., the nipple area, to ensure proper transmission of acoustic waves from transducer 19 to the distal-most portion of breast tissue 22 with a minimum of impedance mismatch. Gel pad 30 also provides attenuation of X-ray radiation to reducing overexposure of the tissue near the nipple and outer edges of breast tissue 22. Further details of gel pad 30 are disclosed in the aforementioned U.S. patent application Ser. Nos. 08/145,958 and 08/277,894.

Because the source of the X-rays is essentially a point source, only X-ray beam 26A is orthogonal to the surface of Bucky 20 and film 28. All other X-ray beams, such as X-ray beam 26B, intersect film 28 at an angle. Previous methods of providing correlation between X-ray and ultrasonic images assume that all X-rays are orthogonal to the image plane, so that, for example, point 32 in the image on X-ray film 28 would correspond to ultrasonic image slice 24 taken from directly above point 32. While this approximation provides good correlation within the resolution of the ultrasonic image scan thickness (i.e., the thickness of the "slices" shown in FIG. 1B), the correspondence degrades the further the distance from orthogonal X-ray beam 26A. Thus, as is seen in FIG. 1B, X-ray 26B passes through tissue 22 at an angle, so that only a small portion of the tissue within ultrasonic slice 24 contributes to the image produced by X-ray 26B.

Figure 3A:
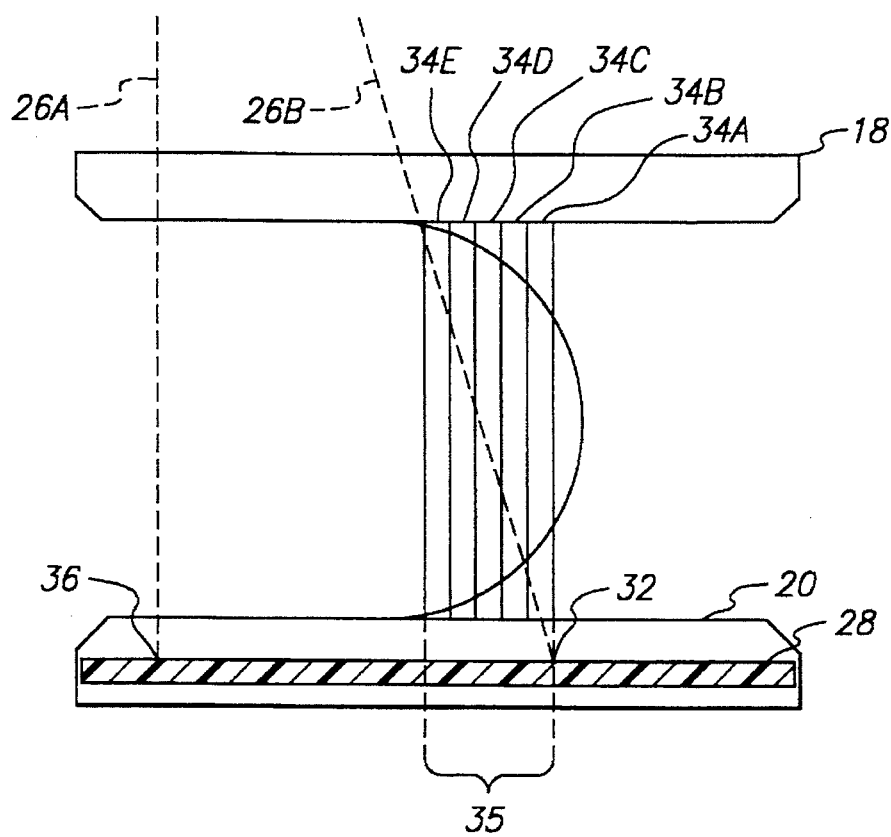
FIG. 3A is a side view of an X-ray "beam" and ultrasonic "slices" of a breast compressed in the sonomammography apparatus of FIG. 1.
Figure 3B:
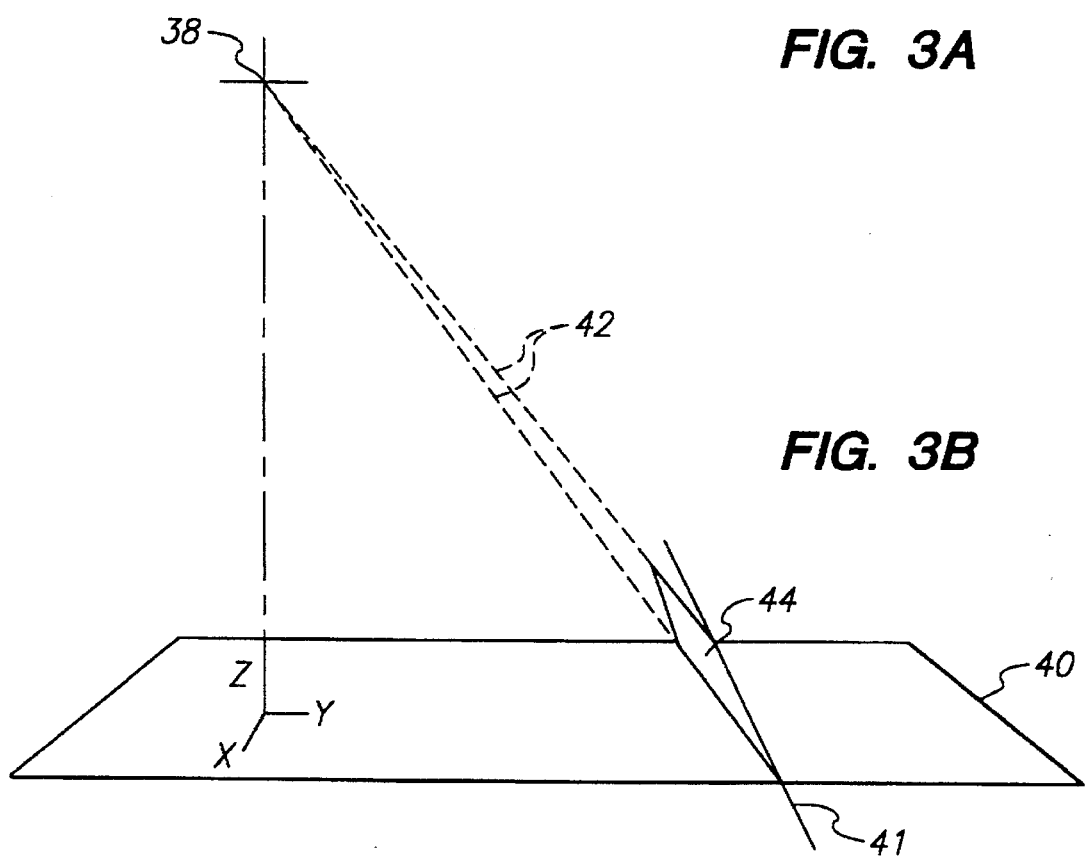
FIG. 3B is an illustration of the tilting of X-ray "planes" caused by spherical spreading of the X-ray beams.

As shown in FIGS. 3A and 3B, X-ray 26B passes through ultrasonic slices 34A through 34E before exposing film 28 at point 32. The angle of X-ray 26B to film 28 and the number of ultrasonic slices that X-ray 26B passes through may be determined by the distance between the X-ray source and film 28 in conjunction with the distance between point 32 on film 28 and point 36 exposed by orthogonal X-ray 26A. To facilitate the following discussion of the methods of the present invention, a coordinate system is shown in FIG. 3B, in which a z-axis passes through the X-ray source and orthogonal to X-ray film 28, an x-axis is co-planer with film 28 and parallel to ultrasonic slices 34A–E, and a y-axis is orthogonal to ultrasonic slices 34A–E.

In FIG. 3B, X-ray beams 42 emanate from point source 38 and travel in essentially straight lines to image plane 40. Group of X-ray beams 42 intersect image plane 40 along straight line 41 to form plane 44. By selecting line 41 such that it is parallel to the plane of ultrasonic slices 34A–E, i.e. parallel to the x-axis, all of X-rays 42 passing through line 41 also pass through the same set of ultrasonic slices. Thus, which ultrasonic slices to correlate to the X-ray image may be determined by first reconstructing X-ray plane 44 and then identifying a single X-ray beam from the group of beams 42 passing through that X-ray plane (and line 41).

Referring still to FIGS. 3A and 3B, the distances between points 32 and 36 on film 28, between Bucky 20 and the X-ray source, and between Bucky 20 and compression plate 18 must be known or measured so that the slope of X-ray 26B may be determined; the slope being given by:

$$\text{slope} = \frac{\text{distance from source to Bucky}}{\text{distance between points 32 and 36}} \qquad (1)$$

From the slope, horizontal extent 35 of X-ray 26B as it passes through breast tissue 22 is given by:

$$\text{extent} = \frac{\text{height of compression plate}}{\text{slope of X-ray beam}} \qquad (2)$$

Any sonogram having an extent along the y-axis which overlaps horizontal extent 35 of X-ray beam 26B contains ultrasonic data from tissue through which X-ray beam 26B has passed, and therefore is to be included in the ultrasonic data correlated to point 32 on film 28.

Figure 4A:
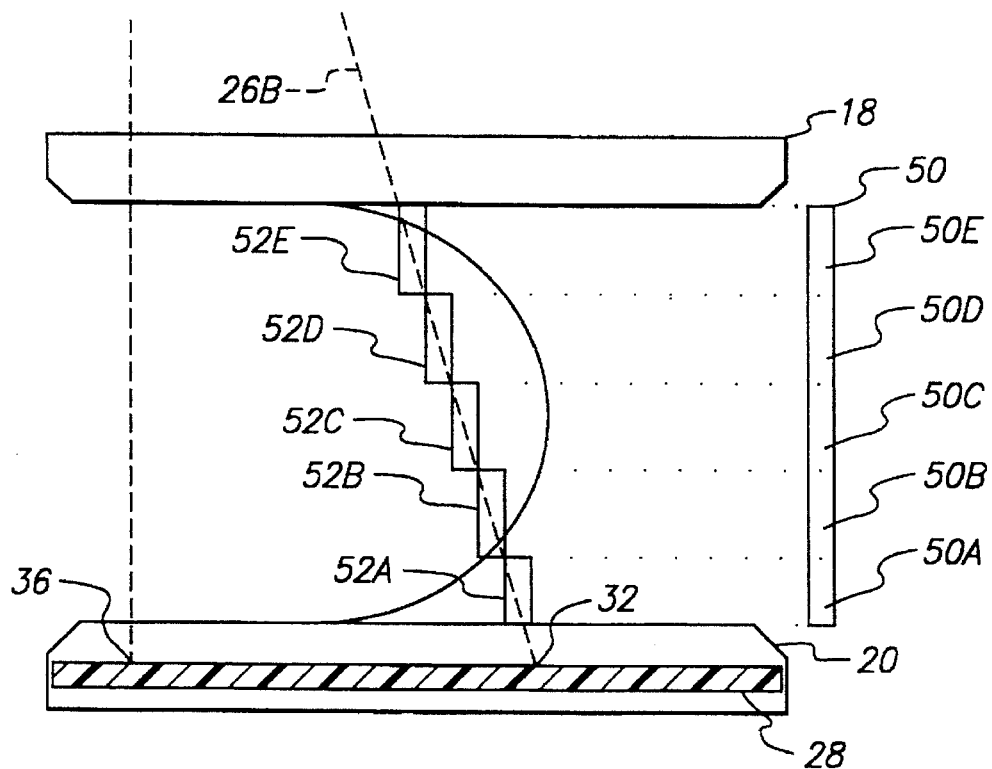
FIGS. 4A and 4B are alternative embodiments of methods in accordance with the present invention for correlating X-ray image data to ultrasonic image data.
Figure 4B:
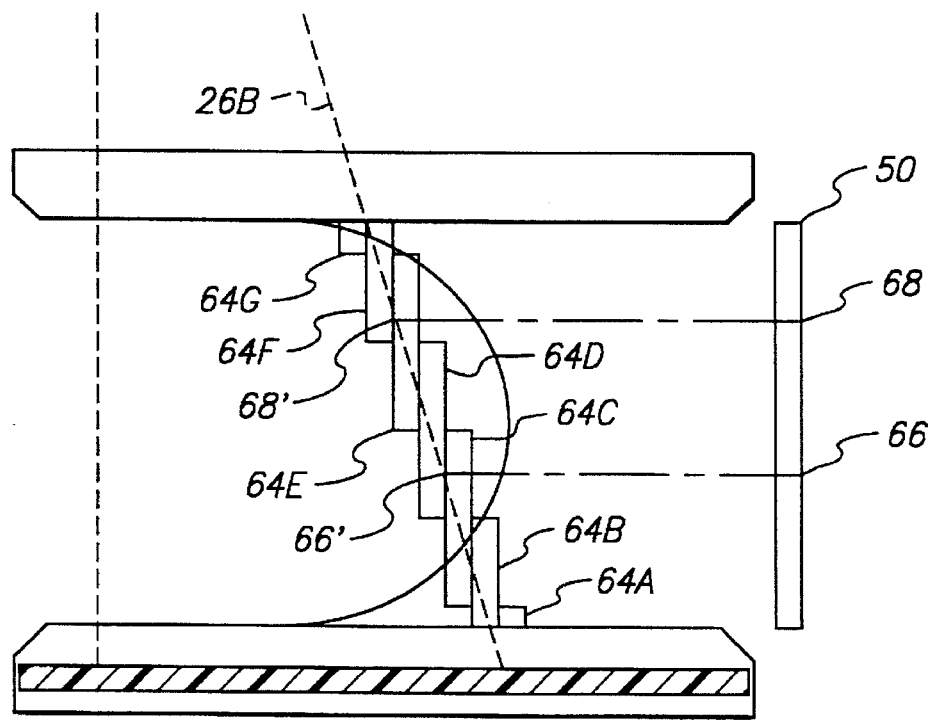

FIGS. 4A and 4B illustrate two alternative methods for constructing composite sonogram 50 corresponding to point 32 on film 28 made by X-ray beam 26B. In the method of FIG. 4A, the composite sonogram is constructed by copying the portion of each sonogram slice that X-ray 26B passed through. For example, sonogram portion 50E corresponds to that portion of sonogram slice 52E that X-ray beam 26B passed through, and is copied into composite slice 50. Similarly, slice portions 52A through 52D are also copied to corresponding portions 50A through 50D to complete composite slice 50. If X-ray beam 26B passes through two horizontally adjacent cubes of FIG. 2, the cube whose center is closer to the trajectory of X-ray beam 26B is copied to composite slice 50. Listing 1 provides illustrative pseudocode for constructing composite ultrasound image 50. The process of determining what ultrasonic data to copy to composite slice 50 is analogous to the process of determining which pixels to illuminate on a CRT display when scan converting a line segment in computer graphics applications. Thus a slightly modified scan conversion

```
delta_y = height of one pixel in composite image
delta_x = delta_y/slope x = coordinate of point on x-ray image
y = height of Bucky while y <= height of compression plate {
    slice = first slice
    while x not in slice, slice = next slice copy row y of slice to row y of composite x = x + delta_x
    y = y + delta_y
}
```

Listing 1 algorithm may be used to quickly and efficiently construct composite sonogram 50. A detailed discussion of scan line conversion techniques is provided in *Computer Graphics*, James Foley et al., $2^{nd}$ Ed., Addison-Wesley Publishing Company, Chapter 3, which is incorporated herein by reference.

Although, the method of FIG. 4A is computationally uncomplicated, a potentially more representative ultrasonic image may be obtained by the method of FIG. 4B. In the method of FIG. 4B, each point in composite sonogram 50 is determined by interpolating the data from the two ultrasonic slices on either side of X-ray 26B. For example, data point 66 in composite image 50 corresponds to location 66' on X-ray beam 26B. Location 66' is on the boundary between ultrasonic slices 64C and 64D so that the data of slices 64C and 64D contribute equally to composite image data point 60. In contrast, location 68', which corresponds to composite image data point 68, X-ray beam 26B is closer to the center line of ultrasonic slice 64E than to the centerline of slice 64F.

Therefore, the data of ultrasonic slice 64E is weighted more heavily than the data of slice 64F in determining a value for composite image point 68.

Still referring to FIG. 4B, let $d_1$ represent the horizontal distance between point 68' on the trajectory of X-ray 26B and the center of slice 64E and $d_2$ represent the horizontal distance between point 68' and the center of slice 64F. Then the value of pixel 68 may be calculated from:

$$w_1 = d_1/(d_1+d_2) \qquad (3)$$

$$w_2 = d_2/(d_1+d_2) \qquad (4)$$

$$P_{68} = w_1 \cdot P_{64E} + w_2 \cdot P_{64F} \qquad (5)$$

where $P_{68}$ is the value of the output pixel in composite image 50, and $P_{64D}$ and $P_{64E}$ represent image values from a corresponding row of ultrasonic slices 64D and 64E respectively. Listing 2 provides illustrative pseudocode for generating pixels in output composite image 50 by using equations (3), (4) and (5) to linearly interpolate between ultrasonic slices.

FIG. 4B is a two dimensional illustration depicting representative ultrasonic slices and X-ray beams. However, the ultrasonic data comprises a volume sampling in three dimensions, each sample representing the amount of ultrasonic energy reflected by corresponding locations in tissue being examined. Furthermore, X-ray beam 26B intersects slices 64A–E at an angle in both the xy and yz planes. Therefore, the interpolation, or more properly, the resampling, of the ultrasonic data must be done in three dimensions. A general discussion of one dimensional resampling techniques and algorithms, and extensions to higher dimensions, is provided in chapters 4 and 5 of *Digital Image Warping*, George Wolberg, IEEE Computer Society Press, 1990, which are incorporated herein by reference.

Figure 5A:
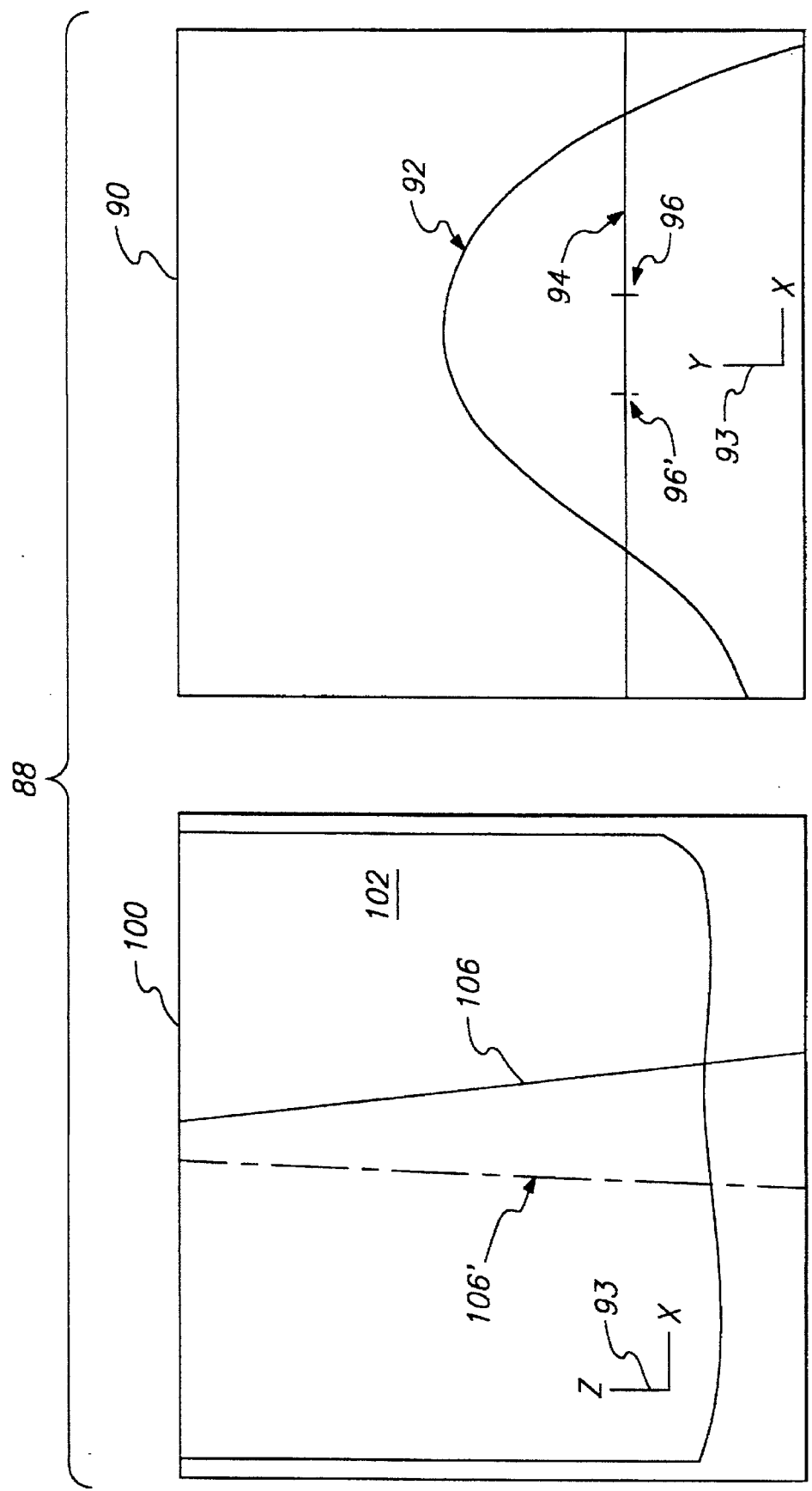
FIGS. 5A and 5B are illustrative displays showing the correlation of X-ray and ultrasonic image data.

Referring now to FIG. 5A, an illustrative user interface 88 for viewing the correlated radiographic and ultrasonic information is described. User interface 88 may comprise a standard display screen, and provides a

```
delta_y = height of one pixel in composite image
delta_x = delta_y/slope x = coordinate of point in x-ray image
y = height of Bucky while y <= height of compression plate {
    slice1 = first slice
    slice2 = second slice while x not between slice1 and slice2 {
        slice1 = slice2
        slice2 = next slice
    } d1 = x - center of slice1
    d2 = center of slice2 - x w1 = d1/(d1 + d2)
    w2 = d2/(d1 + d2)

output row = w1 * slice1 data
               + w2 * slice2 data x = x + delta_x
    y = y + delta_y
}
```

Listing 2 graphical user interface for a general purpose computer such as those manufactured by Apple Computer, Cupertino, Calif.

or International Business Machines, Armonk, N.Y., or Packard-Bell Incorporated, Sacramento, Calif.

Radiographic data corresponding to an X-ray exposure of breast tissue 92 is displayed in window 90. Radiographic data 92 may be obtained by digitizing an image on X-ray film, or may be directly obtained by a digital X-ray receptor, as described hereinabove. Coordinate axes 93 correspond to the axes of FIG. 3B. Cursor 94 is provided which may be repositioned in the y-direction by using a mouse, joystick or other pointing device. The position of cursor 94 along the y-axis is used to determine the location of line 41 of FIG. 3B, and therefore determines X-ray beam plane 44. Composite ultrasonic image 50 of FIGS. 4A or 4B corresponding to X-ray beam plane 44 may then be displayed in window 100.

Cursor 106 models the trajectory of a single X-ray beam through the tissue represented by ultrasonic data 102. Cursor 106 is linked to the position of cursor 94 and cross hair 96 over X-ray image 92. For example, a user may move cross hair 96 to the position indicated by cross hair 96' which in turn causes cursor 106 to move to 106'. In one embodiment of the present invention, linkage between cross hair 96 and cursor 106 is bidirectional, so that the user may directly reposition cursor 106 and the position of cross hair 96 will be updated accordingly. Thus, a clinician may position cursor 94 and cross hair 96 over a suspicious looking location on X-ray image 92 and cursor 106 will indicate ultrasonic data corresponding to the suspicious location in X-ray image.

Figure 5B:
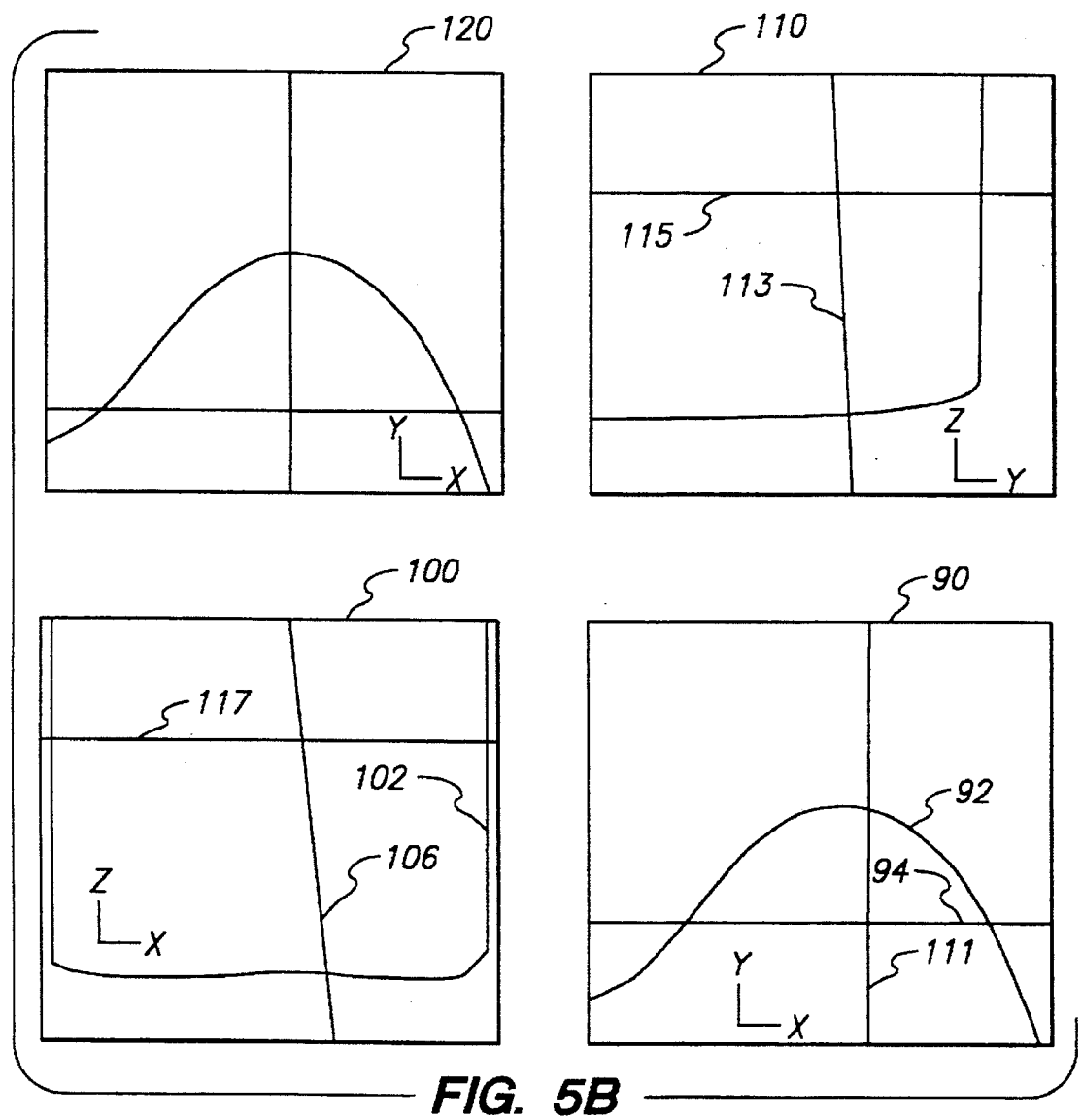

Although cursor 94 and cross hair 96 are oriented horizontally and vertically in window 90, their orientations may be reversed. Composite ultrasonic image 102 then represents an ultrasonic slice parallel to the y-axis instead of parallel to the x-axis. Alternatively, multiple windows may be used to display multiple slices of the ultrasonic data as shown in FIG. 5B, wherein windows 90 and 100 display X-ray and ultrasonic imagery as before. However, cross hair 96 is replaced by cursor 111. The display is augmented by including additional ultrasonic slices of the tissue in windows 110 and 120. The image of window 110 comprises ultrasonic data in a slice parallel to the y-axis and is determined by the location of cursor 111 in window 90. The position of cursor 111 and cursor 113 are linked in a manner similar to the linkage between cursor 106 and cross hair 96 described herein above. Additional cursors 115 and 117 are provided in windows 100 and 110 to select a slice of ultrasonic data orthogonal to the z-axis. In this manner, ultrasonic images corresponding to a top view, a side and a front elevation corresponding to a particular point on the X-ray imagery of window 90 may be provided.

To correlate the ultrasonic data to an X-ray image, the relative location and orientation of X-ray film 28, Bucky 20, and X-ray source 38 of FIGS. 3A and 3B must be known or determined. Preferably, the location and orientation of these items is known based on the design and construction of the mammography apparatus itself. However, for various reasons this manufacturing data may be unavailable. A method of obtaining this information is therefore described.

Figure 6A:
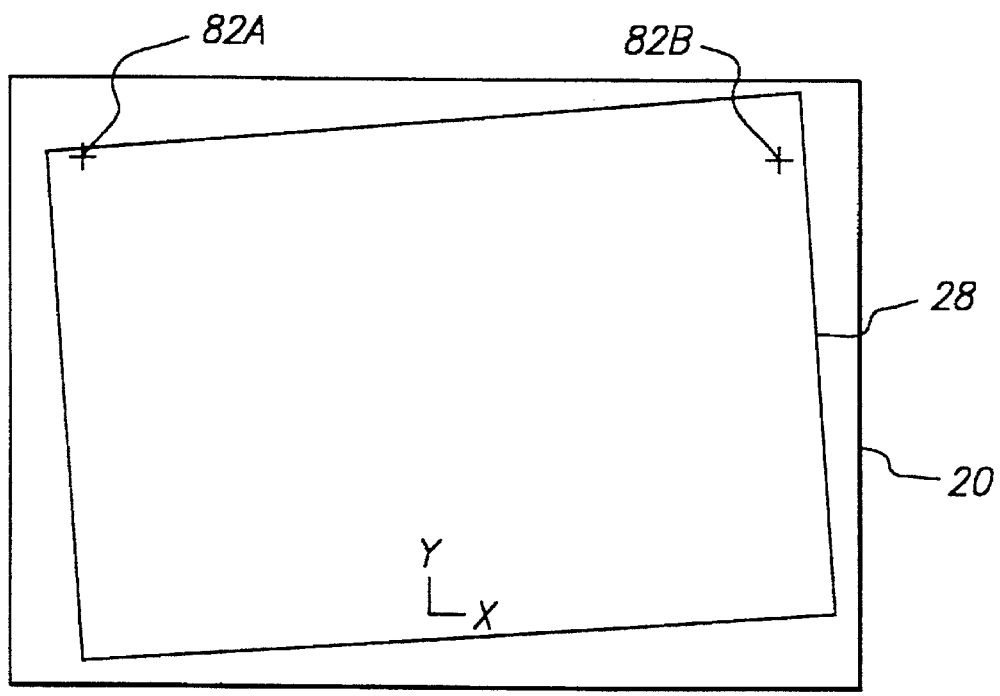
FIGS. 6A and 6B are, respectively, a top view of a film holder illustrating misalignment between the film holder and the X-ray film, and a detailed side elevation of an illustrative embodiment of an apparatus for providing registration between X-ray film and a Bucky.
Figure 6B:
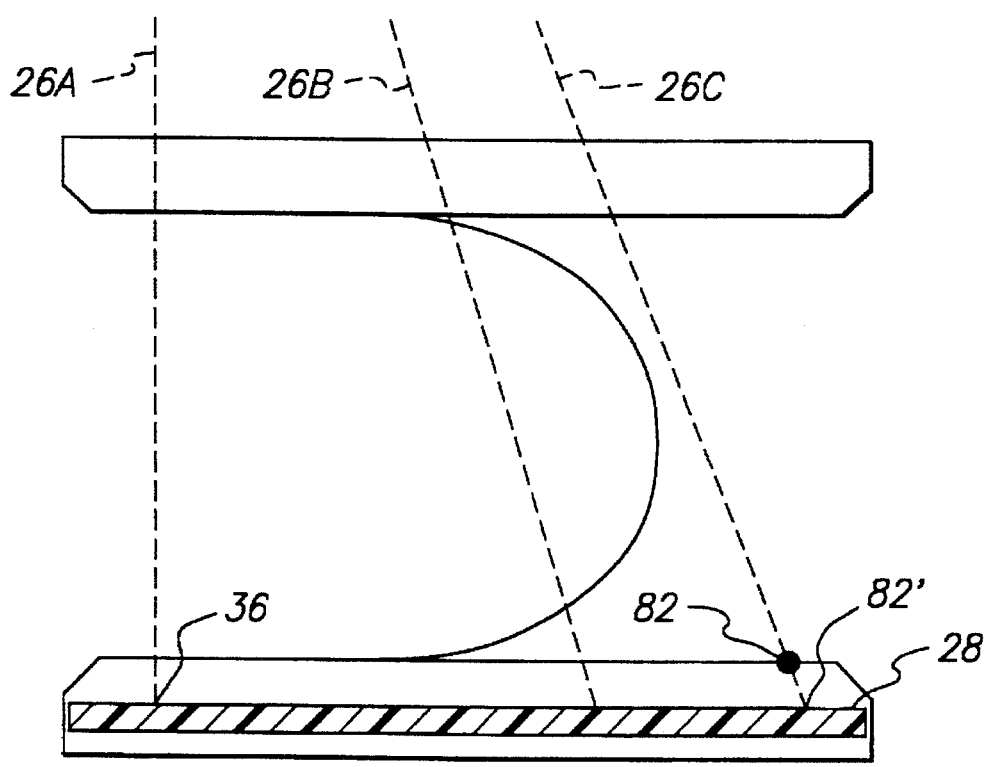

Referring to FIG. 6A, a plan (i.e., overhead) view of X-ray film 28 and film holder 80 is shown. Applicants have determined that film 28 may not be aligned with film holder 80, and hence, may not be aligned with Bucky 20. To provide registration between Bucky 20 and an image on X-ray film 28 reference points 82A and 82B are permanently affixed to Bucky 20. Reference points 82A and 82B are made of a suitable X-ray opaque material, for example, lead, and are preferably embedded in the surface of Bucky 20 during its manufacture. Alternatively, reference points 82A and 82B may be glued or otherwise affixed to the surface of Bucky 20 after manufacture. As shown in FIG. 6B, reference point 82 should be located near the edges of Bucky 20 so as to preclude interference with the X-ray image of the breast tissue. The size, shape, and spacing of reference points 82A and 82B are selected to minimize registration errors.

Since the location of the reference points are known with respect to the axes of Bucky 20, their shadows in the digital X-ray data may be used to align the X-ray data with the sonogram data. For example, when the X-ray data is first displayed on the display of FIGS. 5A and/or 5B, a doctor or technician may invoke an alignment procedure through a menu selection or by pressing a programmable function key. The technician then uses the mouse or other input device to indicate the location of the reference markers in the X-ray data. Alternatively, image processing techniques may be used to automatically identify and locate the reference mark shadows in the X-ray data. Using the location of the reference mark shadows in the X-ray data, and the absolute location of the reference marks which may be input during system calibration, the display processor warps the X-ray data so that the displayed X-ray and ultrasonic images are aligned.

Figures 7A, 7B:
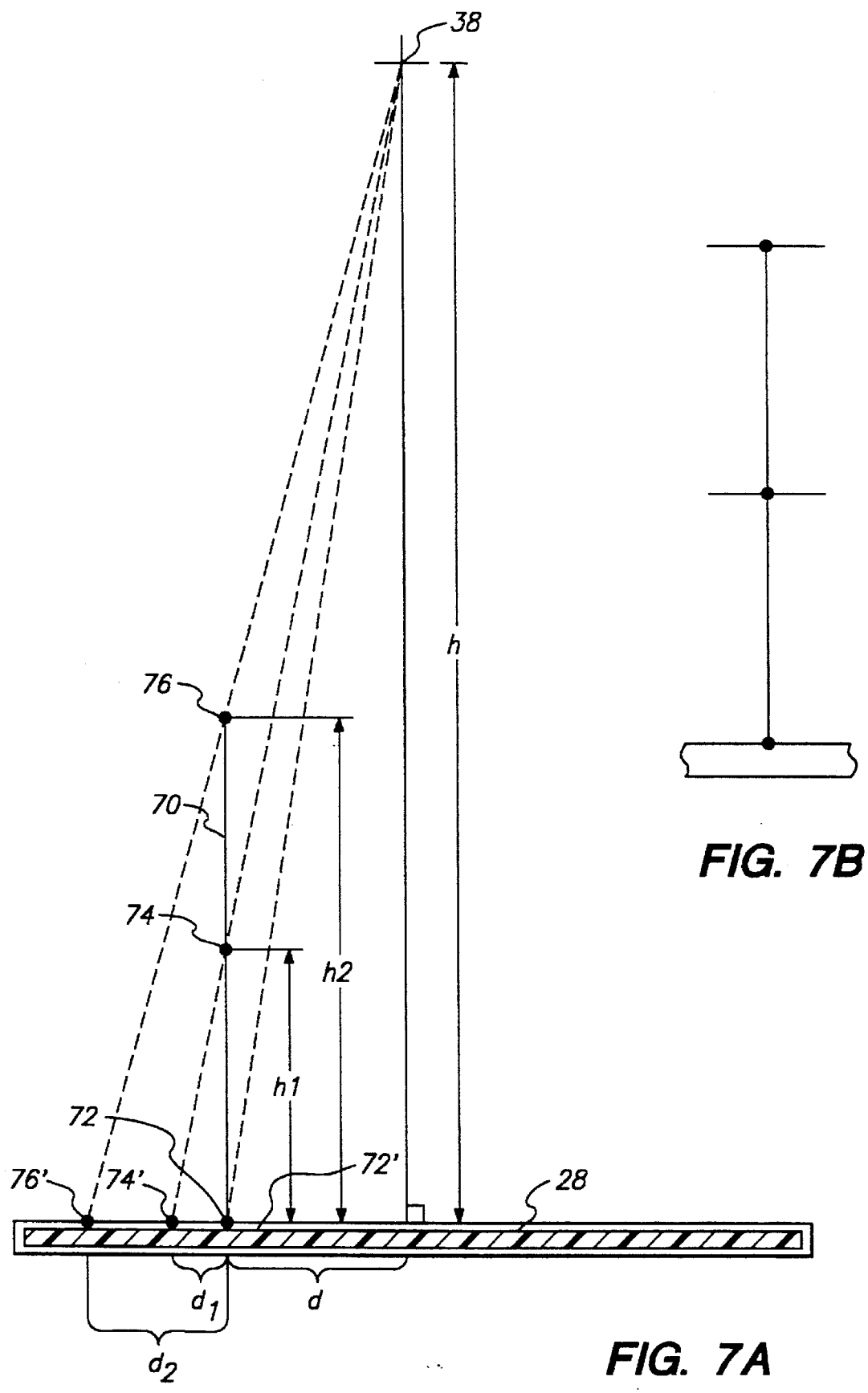
FIGS. 7A, 7B, and 7C are, respectively, a schematic representation of a technique used to determine the location of the X-ray source, a detail of an illustrative apparatus used to determine the location of the X-ray source, and a plan view of the technique of FIG. 7A.

With respect to FIGS. 7A and 7B, a method of determining the location of X-ray source 38 relative to the surface of film 28 is discussed. Gauge 70 is used which comprises several X-ray opaque reference points 72, 74, and 76 which are aligned vertically. For example, gauge 70 may comprise three wires or lead pellets embedded in an X-ray transparent plastic (e.g., lucite sheets) at different heights (h1 and h2). Gauge 70 is positioned at a known location on Bucky 20 and an X-ray is taken. Reference points 72, 74 and 76 cast corresponding shadows at locations 72', 74' and 76' on X-ray film 28, which are separated by distances d1 and d2. By measuring the distances h1, h2 and d1, d2 the height h of X-ray source 38 above Bucky 20 may be calculated from:

$$h = \frac{h_1 h_2 (d_2 - d_1)}{(h_1 d_2 - h_2 d_1)} \quad (6)$$

Figure 7C:
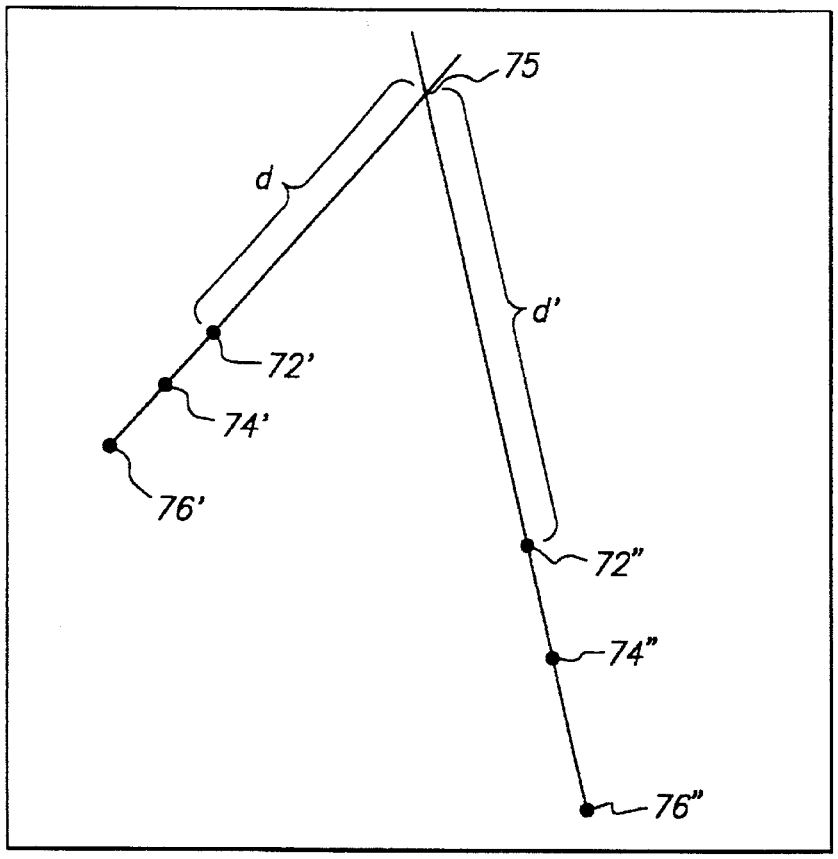

As shown in FIG. 7C, an extension of a line from point 76' through point 72' passes through the origin of the coordinate system, and the distance d to the origin, as measured from point 72' may be calculated from:

$$d = \frac{d_1 d_2 (h_2 - h_1)}{(h_1 d_2 - h_2 d_1)} \quad (7)$$

Preferably the above procedure is repeated several times with gauge 70 located at different positions on Bucky 20 and equations (7) and (8) calculated for each exposure. Alternatively, a gauge may be used which has multiple "stacks" of reference points so that multiple calculations may be obtained from a single X-ray exposure. A least-squared-error procedure is then used to determine the best value for the height of X-ray source 38. The location of coordinate system origin 75 is also be determined by intersecting the line through points 72', 74' and 76', with a line through points 72", 74", and 76" which correspond to another exposure with gauge 70 in a different location on Bucky 20.

Figure 8A:
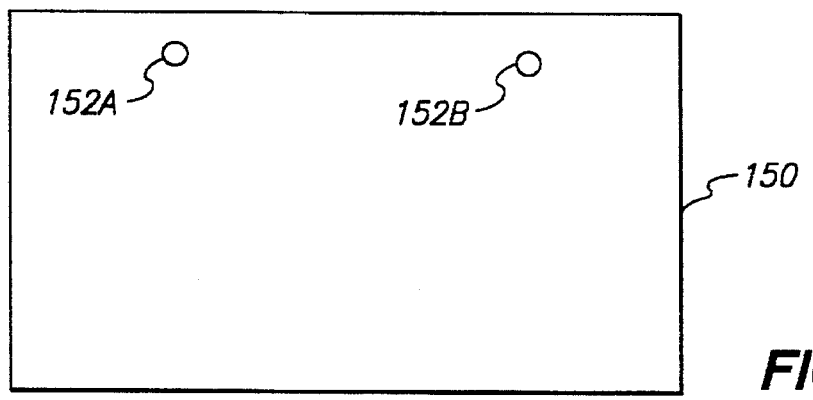
FIGS. 8A and 8B are top views of calibration plates used to determine the location of the X-ray source.
Figure 8B:
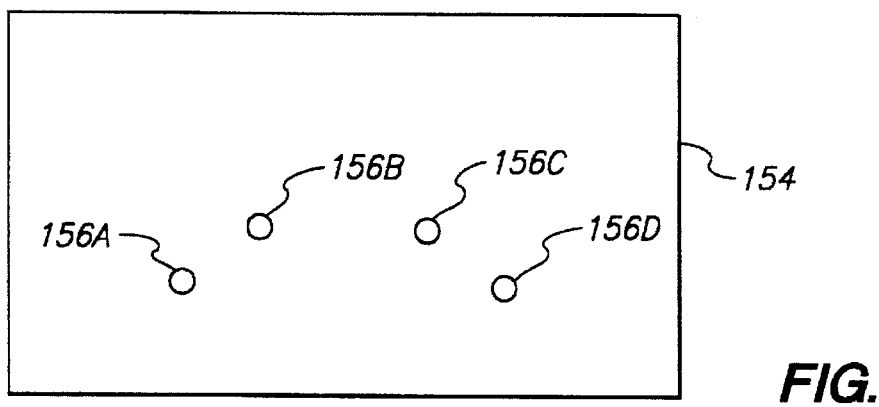
Figure 8D:
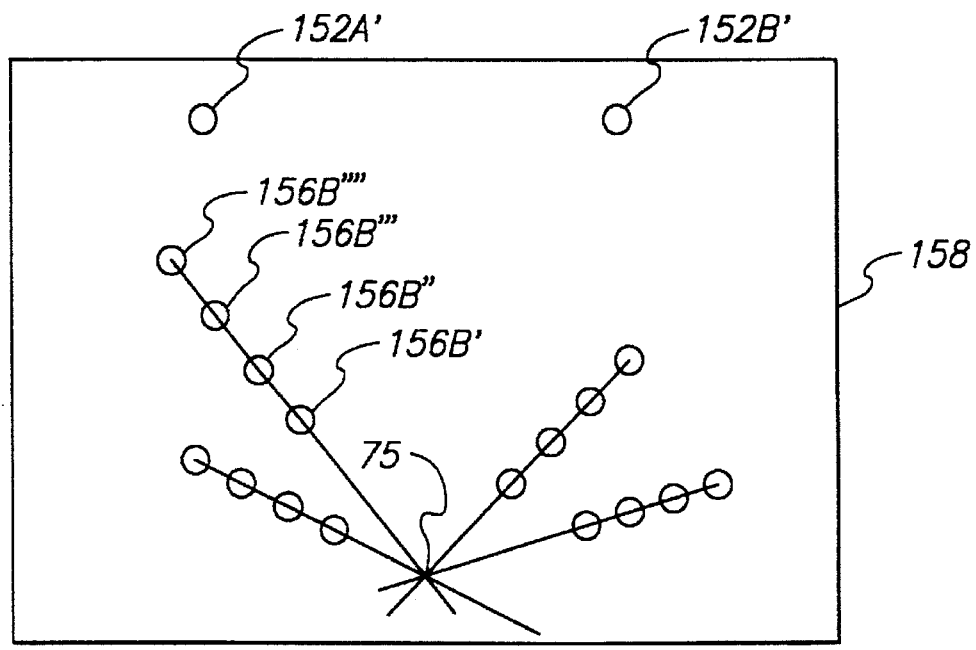
FIG. 8D shows an X-ray image resulting from the calibration procedure.
Figure 8C:
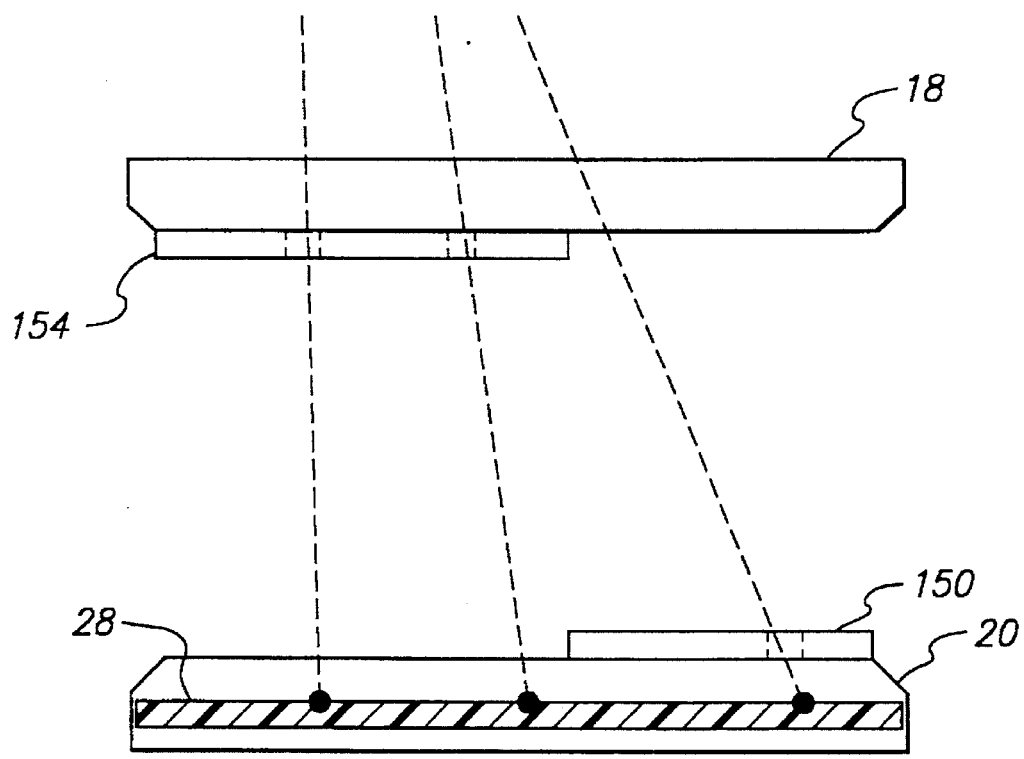
FIG. 8C is a side elevation showing the plates during the calibration procedure.

Referring now to FIGS. 8A-D, an alternative method for determining the location of X-ray source 38 and coordinate origin 75 is described. Plate 150 is attached to the upper surface of Bucky 20 along its rear edge, and has two small holes or apertures 152A and 152B cut through it. Plate 154 has four small holes 156A through 156D and is attached to compression plate 18 along its front edge. Plates 150 and 154 are both prepared of a X-ray opaque material, such as 0.020"–0.025" thick brass plate. As shown in FIG. 8C, plates 150 and 154 overlap so that only those X-ray beams which pass through holes 152A, 152B, and 156A–D expose X-ray film 28.

A first exposure is made with compression plate 18 at its lowest position. Several more exposures are then taken with compression plate 18, and hence plate 150, at different known heights above Bucky 20. This procedure results in an X-ray image similar to that shown in FIG. 8D. Because holes 152A and 152B remain fixed throughout the calibration procedure, they each create a single point (152A' and 152B') on X-ray image 158. However, apertures 156A, 156B, 156C, and 156D create multiple points on X-ray image 158, each point corresponding to an exposure at a different height of compression plate 18. For example, hole 156B exposes points 156B', 156B", 156B"', and 156B"" on X-ray image 158.

Similar to the calibration procedure discussed in conjunction with FIG. 7, the points on X-ray image 158 may be used to calculate the locations of X-ray source 38 and coordinate origin 75. After determining the location of coordinate origin 75, by drawing lines through each series of exposed points as shown in FIG. 8D, the distance from the origin to each point is measured. Linear regression may be used to determine the linear relationship between the measured distances and the heights of Bucky 20, and from this relationship, the height of the X-ray source may be calculated.

While the illustrative embodiments provided herein refer to mammography equipment that generates X-ray films, it will of course be understood by one familiar with radiology that digital (filmless) X-ray systems could be employed as well. It is sufficient for purposes of practicing the present invention that X-ray radiation emitted from an X-ray source pass through biological tissue and form an image in a receptor, whether an X-ray film or a digital X-ray receptor. Commercially available mammography equipment that may be augmented in accordance with the present invention includes, for example, the Contour system by Bennett X-ray Technologies, Inc., Copiague, N.Y., the AVIVA system available from Kramex, Saddle Brook, N.J., and the LORAD DSM system, available from Lorad, Danbury Conn.

One potential way of viewing the stored ultrasound image data is similar to conventional mammography. Since a volume sampling of the entire breast is stored, it is possible to obtain a two-dimensional projection map of the breast attenuation by interpolating and summing the ultrasonic data along the trajectories of X-ray beams corresponding to pixels in the output image. Such an approach is expected to be useful in breast cancer screening. Alternatively, a three dimensional representation of a region of interest may be displayed, which may be especially useful in analyzing the Doppler or vasculature data.

In addition, methods in accordance with the present invention may also include the steps of processing, storing and manipulating the ultrasound images to enhance the diagnostic capabilities of the stored images, using, for example, noise filtering or digital subtraction techniques.

It will be understood that the foregoing is merely illustrative of the apparatus and methods of the present invention, and that various modifications can be made by those skilled in the art without departing from the scope and spirit of the invention.

What is claimed is:

1. A method for correlating ultrasonic image data and X-ray image data of a biological tissue, the ultrasonic image data and X-ray image data obtained in successive steps while the biological tissue remains immobilized, the X-ray image data including a plurality of X-ray data points and the ultrasonic image data including a plurality of ultrasonic data points, the method comprising steps of:

selecting an X-ray data point from the X-ray image data;
   determining a trajectory of an X-ray beam corresponding to the selected X-ray data point; and
   selecting, based on the trajectory of the X-ray beam, a corresponding ultrasonic data point.

2. The method of claim 1 wherein the X-ray image data defines an X-ray plane and the ultrasonic data points reside in a series of mutually parallel spaced apart planes, the method further comprising steps of:

generating a composite ultrasonic image from the ultrasonic data points by selecting, based on the trajectory of the X-ray beam, a corresponding ultrasonic data point in each one of the series of mutually parallel spaced apart planes; and
   displaying the X-ray image data and the composite ultrasonic image.

3. The method of claim 2 wherein the step of generating the composite ultrasonic image comprises copying to the composite ultrasonic image the corresponding ultrasonic data points in each one of the series of mutually parallel spaced apart planes.

4. The method of claim 2 wherein the step of creating the composite ultrasonic image comprises selecting a corresponding ultrasonic data point by interpolating between ultrasonic data points in adjacent ones of the series mutually parallel spaced apart planes.

5. The method of claim 1 wherein the step of obtaining X-ray image data of the biological tissue comprises:

exposing an X-ray film to X-rays passing through the biological tissue;
   developing the X-ray film to form an X-ray image; and
   digitizing the X-ray image to create X-ray image data representative of the X-ray image.

6. The method of claim 1 wherein the step of obtaining X-ray image data of the biological tissue comprises exposing a digital X-ray receptor to X-rays passing through the biological tissue.

7. A method of correlating ultrasonic image data and X-ray image data of a biological tissue, the X-ray image data obtained using an X-ray source exhibiting point source behavior, the method comprising the steps of:

immobilizing the biological tissue;
   obtaining X-ray image data of the biological tissue;
   obtaining ultrasonic image data of the biological tissue;
   correlating the X-ray image data to the ultrasonic image data by resampling the ultrasonic image data to account for the point source behavior of the X-ray source.

8. The method of claim 7 wherein the biological tissue is immobilized in spaced relation to a reference marker, the step of obtaining the X-ray image data includes obtaining X-ray data points representative of the reference marker, and the ultrasonic image data is obtained with a predetermined spatial relation to the reference marker, the method further comprising a step of aligning the X-ray image data with the ultrasonic image data in accordance with location of the X-ray data points representative of the reference marker and the predetermined spatial relation of the ultrasonic image data to the reference marker.

9. The method of claim 7 wherein the step of correlating the X-ray image data to the ultrasonic image data is based on a predetermined model of the point source behavior of the X-ray source.

10. The method of claim 9 wherein the predetermined model is determined by a series of steps of:

provided a grid of index markers, the grid of index markers elevationally spaced apart in a predetermined relation;

exposing the grid of index markers to X-ray beams emanating from the X-ray source to generate a plurality of X-ray data points in an X-ray receptor, the plurality of X-ray data points representative of the grid of index markers;

computing, based on the relative spacing between the plurality of X-ray data points and the predetermined relation of the index markers, a function representative of a degree of non-orthogonality of the X-ray beams.

11. The method of claim 7 wherein the X-ray image data includes a plurality of X-ray data points and the ultrasonic image data includes a plurality of ultrasonic data points, the step of correlating the X-ray image data to the ultrasonic image data comprising steps of:

selecting an X-ray data point from the X-ray image data;

determining a trajectory of an X-ray beam corresponding to the selected X-ray data point; and selecting, based on the trajectory of the X-ray beam, a corresponding ultrasonic data point.

12. The method of claim 11 wherein the X-ray image data defines an X-ray plane and the ultrasonic data points reside in a series of mutually parallel spaced apart planes, the method further comprising steps of:

generating a composite ultrasonic image from the ultrasonic data points by selecting, based on the trajectory of the X-ray beam, a corresponding ultrasonic data point in each one of the series of mutually parallel spaced apart planes; and displaying the X-ray image data and the composite ultrasonic image.

13. The method of claim 11 wherein the step of generating the composite ultrasonic image comprises copying to the composite ultrasonic image the corresponding ultrasonic data points in each one of the series of mutually parallel spaced apart planes.

14. The method of claim 11 wherein the step of creating the composite ultrasonic image comprises selecting a corresponding ultrasonic data point by interpolating between ultrasonic data points in adjacent ones of the series mutually parallel spaced apart planes.

15. The method of claim 7 wherein the step of obtaining X-ray image data of the biological tissue comprises:

exposing an X-ray film to X-rays passing through the biological tissue;

developing the X-ray film to form an X-ray image; and digitizing the X-ray image to create X-ray image data representative of the X-ray image.

16. The method of claim 7 wherein the step of obtaining X-ray image data of the biological tissue comprises exposing a digital X-ray receptor to X-rays passing through the biological tissue.

17. Apparatus for obtaining correlated ultrasonic images and X-ray images of a biological tissue, the apparatus comprising:

means for immobilizing the biological tissue;

means for obtaining an ultrasonic image of the biological tissue, the ultrasonic image comprising a plurality of ultrasonic data points;

means for obtaining an X-ray image of the biological tissue using an X-ray source;

computing means for correlating a point in the X-ray image to a plurality of ultrasonic data points based on a computed trajectory for an X-ray beam exposing the point in the X-ray image, the computed trajectory for the X-ray beam based on a predetermined model of the X-ray source, the computing means generating a composite ultrasonic image from the correlated ultrasonic data points; and means for displaying the X-ray image and composite ultrasonic image.

18. Apparatus as defined in claim 17 further comprising means for determining the predetermined model of the X-ray source, the X-ray source exhibiting point source behavior, the apparatus comprising a grid of index markers elevationally spaced apart in a predetermined relation.

* * * * *